(12) United States Patent
Morris et al.

(10) Patent No.: US 8,536,527 B2
(45) Date of Patent: Sep. 17, 2013

(54) IMAGING BASED ON COSMIC-RAY PRODUCED CHARGED PARTICLES

(75) Inventors: Christopher L. Morris, Los Alamos, NM (US); Larry Joe Schultz, Los Alamos, NM (US); Jesse Andrew Green, Los Alamos, NM (US); Michael James Sossong, Ramona, CA (US); Konstantin N. Borozdin, Los Alamos, NM (US); Alexei V. Klimenko, Santa Fe, NM (US); Gary Blanpied, Lexington, SC (US); Vladimir Tumakov, Aliso Viejo, CA (US); Kolo Wamba, San Diego, CA (US)

(73) Assignees: Decision Sciences International Corporation, Poway, CA (US); Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 13/061,491

(22) PCT Filed: Aug. 27, 2009

(86) PCT No.: PCT/US2009/055253
§ 371 (c)(1),
(2), (4) Date: Jun. 27, 2011

(87) PCT Pub. No.: WO2010/025300
PCT Pub. Date: Mar. 4, 2010

(65) Prior Publication Data
US 2011/0248163 A1 Oct. 13, 2011

Related U.S. Application Data

(60) Provisional application No. 61/092,372, filed on Aug. 27, 2008, provisional application No. 61/145,091, filed on Jan. 15, 2009.

(51) Int. Cl.
*G01N 23/08* (2006.01)
*G01N 23/00* (2006.01)

(52) U.S. Cl.
USPC .................. 250/307; 250/306; 250/358.1

(58) Field of Classification Search
USPC .............. 250/306, 307, 358.1–360.1, 385.1, 250/395
See application file for complete search history.

(56) References Cited

U.S. PATENT DOCUMENTS

| 7,470,905 B1* | 12/2008 | Goldberg et al. | 250/358.1 |
| 2007/0102648 A1* | 5/2007 | Shpantzer et al. | 250/394 |
| 2008/0315091 A1* | 12/2008 | Morris et al. | 250/307 |

OTHER PUBLICATIONS

Schultz et al, "Statistical Reconstruction for Cosmic Ray Muon Tomography", IEEE Transactions on Image Processing, vol. 16, No. 8, Aug. 2007, p. 1985-1993.*
Hanson et al, "Computed Tomography Using Proton Energy Loss", Phys. Med. Biol, 1981, vol. 26, No. 6, 965-983.*

* cited by examiner

*Primary Examiner* — Robert Kim
*Assistant Examiner* — David E Smith
(74) *Attorney, Agent, or Firm* — Perkins Coie LLP

(57) ABSTRACT

Techniques, apparatus and systems for obtaining tomographic images of a volume of interest by using charged particle tomography detection systems.

17 Claims, 11 Drawing Sheets

IMAGING BASED ON COSMIC-RAY PRODUCED CHARGED PARTICLES

PRIORITY CLAIM

This patent document claims benefits of U.S. Provisional Application No. 61/092,372 entitled "IMAGING BASED ON COSMIC-RAY PRODUCED CHARGED PARTICLES" and filed on Aug. 27, 2008 and U.S. Provisional Application No. 61/145,091 entitled "TOMOGRAPHIC IMAGING USING ENERGY LOSS OF COSMIC-RAY PRODUCED CHARGED PARTICLES" and filed on Jan. 15, 2009, both of which are incorporated by reference as part of this document.

BACKGROUND

This patent document relates to detection of cosmic radiation and imaging based on imaging based on cosmic-ray produced charged particles.

Cosmic ray tomography is a technique which exploits the multiple Coulomb scattering of cosmic ray-produced charged particles (e.g., muons) to perform non-destructive inspection of the material without the use of artificial radiation. The earth is continuously bombarded by energetic stable particles, mostly protons, coming from deep space. These particles interact with atoms in the upper atmosphere to produce showers of particles that include many short-lived pions which decay producing longer-lived muons. Muons interact with matter primarily through the Coulomb force having no nuclear interaction and radiating much less readily than electrons. Such cosmic ray-produced particles slowly lose energy through electromagnetic interactions. Consequently, many of the cosmic ray-produced muons arrive at the earth's surface as highly penetrating charged radiation. The muon flux at sea level is about 1 muon per cm$^2$ per minute. Also at sea level, there exists a flux of cosmic ray generated electrons, from delta ray production (electron knock-out), Bremsstrahlung or the decay of particles in cosmic ray induced showers. The electron flux at sea level is about 1 electron per cm$^2$ per 3 minutes.

As a charged particle such as a muon moves through material, Coulomb scattering off of the charges of sub-atomic particles perturb its trajectory. The total deflection depends on several material properties, but the dominant effect is the atomic number, Z, of nuclei. The trajectories of charged particles (e.g., muons) are more strongly affected by materials that make good gamma ray shielding, such as lead and tungsten, and by special nuclear materials (SNMs), such as uranium and plutonium, than by materials that make up more ordinary objects such as water, plastic, aluminum and steel. Each charged particle (e.g., a muon) carries information about the objects that it has penetrated. The scattering of multiple charged particles (e.g., muons) can be measured and processed to probe the properties of these objects. A material with a high atomic number Z and a high density can be detected and identified when the material is located, inside low-Z and medium-Z matter.

Coulomb scattering from atomic nuclei in a matter results in a very large number of small angle deflections of charged particles as the transit the matter. A correlated distribution function can be used to approximately characterize the displacement and angle change of the trajectory that depends on the density and the atomic charge of the material. As an example, this distribution function can be approximated as a Gaussian distribution. The width of the distribution function is proportional to the inverse of the momentum of the particle and the square root of the real density of material measured in radiation lengths. The correlated distribution function of cosmic ray-produced charged particles (e.g., muons) can provide information on materials in the paths of the charged particles with no radiation dose above the earth's background and proper detection of such cosmic ray-produced charged particles (e.g., muons) can be implemented in a way that is especially sensitive to selected materials to be detected such as good radiation shielding materials.

A charged particle tomography detection system, e.g., a muon tomography detection system, can be configured to perform tomography of a target object under inspection based on scattering of charged particles by the target object and can be used as a portal monitor at various locations, such as border crossing points, ports, roadway checkpoints and other security checkpoints, for detecting certain targeted objects such as smuggled nuclear materials, nuclear and conventional weapons or other contraband. Charged particle tomography detector systems can be used jointly with or an alternative to other nuclear material detectors such as gamma or X ray detectors. Gamma and X ray detectors operate by directing Gamma and X ray radiation to a target and measuring penetrated Gamma and X ray radiation. Shielding of nuclear materials can reduce the count rates in the Gamma and X ray detectors and reduce the detection performance of Gamma and X ray detectors. Charged particle tomography detection systems can be configured to detect shielded nuclear materials and objects.

SUMMARY

This document provides techniques, apparatus and systems for obtaining tomographic images of a volume of interest by using charged particle tomography detection systems.

In one aspect, a method for sensing a volume exposed to charged particles includes measuring energy loss of charged particles that enter and penetrate the volume or are stopped inside the volume without penetrating through the volume; based on the measured energy loss, determining a spatial distribution of the charged particles that enter and penetrate the volume or are stopped inside the volume without penetrating through the volume; and using the spatial distribution of the energy loss of the charged particles to reconstruct the three-dimensional distribution of materials in the inspection volume.

In another aspect, a tomography inspection system is provided to include a first set of position sensitive detectors located on a first side of an object holding area to measure positions and directions of incident charged particles entering the object holding area; a second set of position sensitive detectors located on a second side of the object holding area opposite to the first side to measure positions and directions of outgoing charged particles exiting the object holding area, or the absence of charged particles that have stopped in the volume; and a signal processing unit to receive data of measured signals of the incoming charged particles from the first set of position sensitive detectors and measured signals of the outgoing charged particles from the second set of position sensitive detectors. The signal processing unit is configured to analyze behaviors of the charged particles caused by interactions with materials within the object holding area based on the measured incoming and outgoing positions and directions of charged particles to obtain a tomographic profile or the spatial distribution of materials within the object holding area. The signal processing unit is operable to measure energy loss of charged particles that enter the volume and penetrate through the volume, and charged particles that are stopped inside the volume without penetrating through the volume, determine a spatial distribution of the charged particles that enter the volume and penetrate through the volume and charged particles that are stopped inside the volume without penetrating through the volume; and, based on the measured energy loss, using the spatial distribution to reconstruct the spatial distribution of materials within the inspection volume.

In another aspect, a method for sensing a volume exposed to charged particles is provided to include using a first set of position sensitive detectors located on a first side of the volume to measure positions and directions of incident charged particles that penetrate the first set of position sensitive detectors to enter the volume; using a second set of position sensitive detectors located on a second side of the volume opposite to the first side to measure positions and directions of outgoing charged particles exiting the volume or the lack thereof; using measurements made by the second set of position sensitive detectors to determine incident charged particles that enter the volume and penetrate through the volume and charged particles that do not penetrate through the volume to reach the second set of position sensitive detectors; determining energy loss of charged particles that enter the volume and penetrate through the volume and charged particles that are stopped inside the volume without penetrating through the volume; determining a spatial distribution of the charged particles that enter the volume and are stopped inside the volume without penetrating through the volume, based on the measured energy loss; and using the spatial distribution of charged particles that enter the volume and are stopped inside to reconstruct the spatial distribution of materials in the inspection volume.

In another aspect, a method for sensing a volume exposed to charged particles is provided to include measuring energy loss of charged particles that enter the volume and are stopped inside the volume without penetrating through the volume; based on the measured energy loss, determining a spatial distribution of the charged particles that enter the volume and are stopped inside the volume without penetrating through the volume; and using the spatial distribution to reconstruct the three dimensional spatial distribution of materials in the volume according to their respective densities and atomic numbers. From this spatial distribution, objects can be detected according to their atomic number and density.

In another aspect, a method for sensing a volume exposed to charged particles is provided to include measuring energy loss of charged particles that enter the volume and are stopped inside the volume without penetrating through the volume; based on the measured energy loss, determining a spatial distribution of the charged particles that enter the volume and are stopped inside the volume without penetrating through the volume; and using the spatial distribution to detect presence of one or more low density materials with low atomic numbers.

In another aspect, a tomography inspection system is provided to include a first set of position sensitive detectors located on a first side of an object holding area to measure positions and directions of incident charged particles towards the object holding area; a second set of position sensitive detectors located on a second side of the object holding area opposite to the first side to measure positions and directions of outgoing charged particles exiting the object holding area; and a signal processing unit to receive data of measured signals of the incoming charged particles from the first set of position sensitive detectors and measured signals of the outgoing charged particles from the second set of position sensitive detectors. The signal processing unit is configured to analyze scattering behaviors of the charged particles caused by scattering of the charged in the materials within the object holding area based on the measured incoming and outgoing positions and directions of charged particles to obtain a tomographic profile or the spatial distribution of scattering centers within the object holding area. The signal processing unit is operable to measure energy loss of charged particles that enter the volume and are stopped inside the volume without penetrating through the volume, determine a spatial distribution of the charged particles that enter the volume and are stopped inside the volume without penetrating through the volume, based on the measured energy loss, and use the spatial distribution to reconstruct the three dimensional spatial distribution of materials in the volume according to their density and atomic number. From this spatial distribution, objects can be detected according to their atomic number and density. In one implementation, this can be used to detect presence of one or more low density materials with low atomic numbers.

In another aspect, a method for sensing a volume exposed to charged particles includes using a first set of position sensitive detectors located on a first side of the volume to measure positions and directions of incident charged particles that penetrate the first set of position sensitive detectors to enter the volume; using a second set of position sensitive detectors located on a second side of the volume opposite to the first side to measure positions and directions of outgoing charged particles exiting the volume; using measurements made by the second set of position sensitive detectors to determine incident charted particles that enter the volume and do not penetrate through the volume to reach the second set of position sensitive detectors; determining energy loss of charged particles that enter the volume and are stopped inside the volume without penetrating through the volume; determining a spatial distribution of the charged particles that enter the volume and are stopped inside the volume without penetrating through the volume, based on the measured energy loss; and using the spatial distribution to reconstruct the three dimensional spatial distribution of materials in the volume according to their density and atomic number. From this spatial distribution, objects can be detected according to their atomic number and density. In one implementation, this can be used to detect presence of one or more low density materials with low atomic numbers inside the volume.

In another aspect, a tomography inspection system is provided to include a first set of position sensitive charged particle detectors located on a first side of an object holding area to measure positions and directions of incoming charged particles entering the object holding area; a second set of position sensitive charged particle detectors located on a second side of the object holding area opposite to the first side to measure positions and directions of outgoing charged particles exiting the object holding area; and a signal processing unit to communicate with the first and second set of position sensitive charged particle detectors to receive data of measured signals of the incoming charged particles from the first set of position sensitive charged particle detectors and measured signals of the outgoing charged particles from the second set of position sensitive charged particle detectors, based on the received data, detect an incoming momentum of each incoming charged particle and an outgoing momentum of each outgoing charged particle; and calculate an energy loss based on the detected incoming and outgoing momenta.

In another aspect, a method for obtaining tomographic images of an object under inspection is provided to include detecting an incoming momentum of each incoming charged particles; detecting an outgoing momentum of each outgoing charged particle; calculating an energy loss based on the detected incoming and outgoing momenta; and using the calculated energy loss to reconstruct the three dimensional spatial distribution of materials in the volume according to their density and atomic number. From this spatial distribution, objects can be detected according to their atomic number and density.

In yet another aspect, the information measured in both penetrated charged particles and trapped charged particles of a volume of interest can be used to construct tomographic images of the volume. Based on the measurements of the penetrated and stopped charged particles, the processing unit combines two or three types of measured data of trajectory changes of penetrated charged particles (e.g., penetrated muons), the information on stopped charged particles that are trapped inside the volume of interest (e.g., trapped muons), and the information on energy loss of penetrated charged particles (e.g., penetrated muons) to construct a tomographic image of the volume of interest. This process uses information of different processes inside the volume of interest to improve the fidelity and resolution of the final image for the volume of interest and to reduce the false detection.

These and other aspects are described in greater detail in the drawings, the description and the claims.

DETAILED DESCRIPTION

Figure 1:
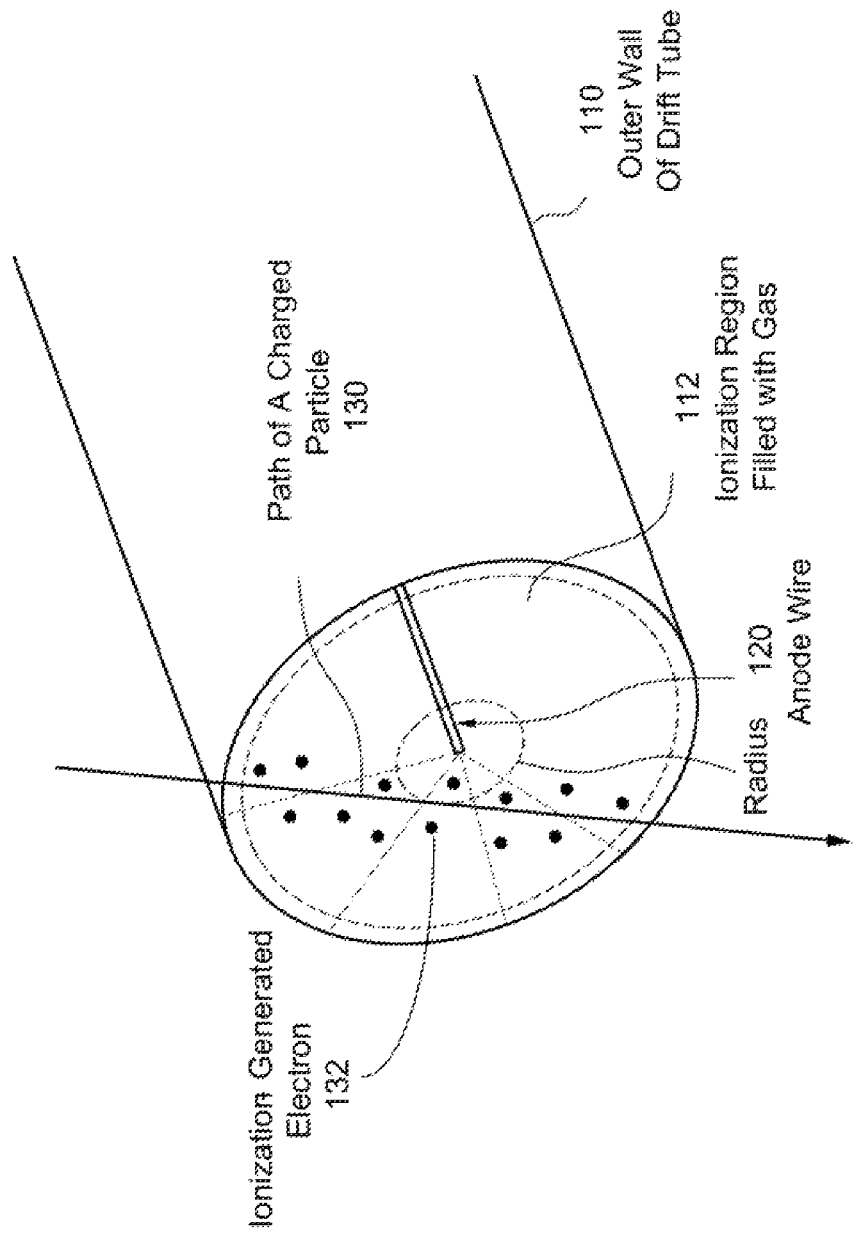
FIG. 1 illustrates operations of an exemplary draft tube gas chamber for detecting charged particles.

The charged particle tomography detection techniques, apparatus and systems described in this application can be implemented to detect the presence of certain objects or materials such as nuclear materials and to obtain tomographic information of such objects in various applications including but not limited to inspecting packages, containers, occupied vehicles at security check points, border crossings and other locations for nuclear threat objects that may range from fully assembled nuclear weapons to small quantities of highly shielded nuclear materials. The approach enables detection of shielded and unshielded nuclear material using a single detector system in a compact configuration to provide a cost effective way for detecting nuclear and other targeted devices and materials.

Background cosmic radiation provides a source that can be used to study the internal structure of objects with no need for additional radiation. Muon tomography (MT) produces 3-dimensional images of the "scattering density," the density weighted by the radiation length of a material. MT can discriminate between general classes of materials (high-, medium-, low-Z) in sub-one minute exposure times in 5 cm voxels. Range radiography, which uses the component of the cosmic ray flux that stops in an object being studied, provides added information and can complement the muon tomography signal in a way that provides information about the material composition of objects. A cosmic ray tracker, which measures the incident particles, adds considerable statistical power to the range information.

Charged particle tomography takes advantage of the constant sea-level flux of charged particles generated via interactions of cosmic radiation with the Earth's atmosphere. Outside the hadronic sector, the muon interacts only via the Coulomb and weak forces, for example. Because of this, it is highly penetrating of matter. These charged particles have an average energy of approximately 3 GeV. For example, most atmospheric muons will penetrate more than a meter of lead. Muons reach the surface with a cosine-squared distribution in zenith. Flux is low at angles off zenith close to 90°, but the average muon angle off zenith is 37.5°.

Features described in this application can be used to construct various charged particle tomography detection systems. For example, a charged particle tomography system can include an object holding area or volume for placing an object to be inspected, a first set of position sensitive charged particle detectors located on a first side of the object holding area to measure positions and directions of incident charged particles towards the object holding area, a second set of position sensitive charged particle detectors located on a second side of the object holding area opposite to the first side to measure positions and directions of outgoing charged particles exiting the object holding area, and a signal processing unit, which may include, e.g., a microprocessor, to receive data of measured signals of the incoming charged particles from the first set of position sensitive charged particles detectors and measured signals of the outgoing charged particles from the second set of position sensitive charged particle detectors.

As an example, each of the first and second sets of charged particle detectors can be implemented to include drift tubes arranged to allow charged particle positional measurements in a first direction and charged particle positional measurements in a second direction different from the first direction. The signal processing unit is configured to analyze scattering behaviors of the charged caused by scattering of the charged particles in the materials within the object holding area based on the measured incoming and outgoing positions and directions of charged particles to obtain a tomographic profile or the spatial distribution of scattering centers within the object holding area. The obtained tomographic profile or the spatial distribution of scattering centers can be used to reveal the presence or absence of one or more objects in the object holding area such as materials with high atomic numbers including nuclear materials or devices, or objects with specific density and atomic number signatures, such as low-Z explosives or other medium- or low-Z contraband.

In addition, electromagnetic showers generated by charged particles, such as high energy electrons interacting with objects within a volume of interest can be characterized at the second set of charged particle detectors. Electrons and positron from the generated electromagnetic showers traverse through the volume and exit the second set of charged particle detectors.

Each position sensitive charged particle (e.g., muon) detector can be implemented in various configurations, including drift cells such as drift tubes filled with a gas which can be ionized by charged particles. Such a system can be implemented to utilize natural cosmic ray-produced charged particles as the source of charged particles for detecting one or more objects in the object holding area. Various features of exemplary charged particle tomography detection systems are described in PCT Application No. PCT/US2007/082573 entitled "Particle Detection Systems and Methods" and filed on Oct. 25, 2007 (PCT Publication No. WO2008/123892), which is incorporated by reference as part of the specification of this application.

In some applications, the particle detection systems can utilize drift tubes to enable tracking of charged particles, such as muons, passing through a volume. However, those skilled in the art would understand that such charge particle detectors can be employed in applications other than cosmic ray-produced charged particle tracking to detect charged particles other than cosmic ray-produced charged particles. These charged particle detectors are applicable to any charged particle from any appropriate source. For example, muons can be produced by cosmic rays or a low intensity beam of muons from an accelerator.

Cosmic ray-produced charged particles can provide information with no radiation dose above the earth's background and proper detection of such cosmic ray-produced charged particles can be implemented in a way that is especially sensitive to good shielding materials. A charged particle detection system can be configured to perform tomography of a target object under inspection based on scattering of charged particles by the target object. The system can be configured to perform tomography to localize scattering (RC & LS). The tomographic position resolution can be expressed approximately as follows:

$$\Delta x = \theta_{RMS} L$$

where:

$\theta_{RMS}$=the root-mean-square (rms) of the scattering angle, and

L=the size of the volume under the detection by the detection apparatus.

For example, for an exemplary rms scattering angle of 0.02 radian and an apparatus size of 200 cm, the tomographic position resolution is 0.02×200 cm=4 cm.

In one approach, the angular resolution is determined by the following equation based on the Poisson statistics:

$$\frac{\Delta \theta}{\theta} = \frac{1}{\sqrt{2N}}$$

where:

θ=the rms scattering angle,

N=number of cosmic ray-produced charged particles such as muons passing through a region of interest.

For example, the angular resolution for N=100 (corresponding to a 10×10 cm² resolution element after one minute of counting is Δθ=0.07θ.

Table 1 illustrates theoretical energy loss rate (dE/dx) and radiation length (X) for various materials. One minute of counting distinguishes a 10 cm cube of iron from a 10 cm cube of lead at 6 standard deviations on the basis of their different values of X.

TABLE 1

| Material | dE/dx MeV-cm²/gm | X cm |
|---|---|---|
| H₂O | 2.06 | 36 |
| Fe | 1.87 | 1.76 |
| Pb | 1.54 | 0.56 |

Tomographic methods, designed to construct an image or model of an object from multiple projections taken from different directions, can be implemented in the cosmic ray system to provide a discrete tomographic reconstruction of the volume of interest based on the data provided by the charged particles. In some implementations, Monte Carlo simulation techniques can be used to study applications and shorten scanning times. Other stochastic processing methods may also be used in implementing the charged particle tomographic imaging described in this application.

The cosmic ray radiography function of the particle detection systems of the embodiments can be more readily understood with reference to examples of detection systems adapted to detect charged particles.

Drift tubes are gas chambers designed for detecting moving charged particles. Each drift tube includes a gaseous medium enclosed inside a chamber that can be ionized by a moving charged particle passing through the gaseous medium. An anode wire conductor is placed near the center of the drift tube and the wall of the drift tube is grounded to establish an electric field directed from anode wire conductor towards the wall. An incoming charged particle ionizes the gas molecules of the gas medium to produce free electrons that are accelerated by the electric field towards the anode wire conductor. The drift time for such an electron to reach the anode wire conductor can be measured. Along the path of the incoming charged particle inside the drift tube, the drift times of electrons generated at different locations of the path of the charged particle are measured and are used to determine the track of the charged particle inside the drift tube. One applications for drift tubes is detection of charged particles (e.g., muons) by using one or more arrays of drift tubes.

FIG. 1 illustrates operations of an exemplary draft tube gas chamber for detecting charged particles. The drift tube in this example is a cylindrical tube formed by outer cylindrical wall 110 and is filled with a detector gas 112 such as Argon-Isobutane 230 to enable detection of the cosmic ray-produced charged particles, such as muons. A central anode wire 120 extending along the length of the cylindrical tube is provided to electrically biased at a higher potential than the outer wall 110 to produce a positive voltage (e.g., 2-3 kV or higher) to generate a high-voltage static field inside the tube directing along radial directions from the anode wire 120 towards the wall 110 in an ionization region 112 inside the outer wall 110. When a charged particle 130 enters the tube and interacts with gas atoms in the region 112, multiple electrons 132 are liberated from those gas atoms. The static field causes the "string" of electrons to drift toward the positively charged anode wire 120. The anode wire 120 can be very thin, e.g., 0.001" in diameter, thus creating a very high electric field near the wire 120 to produce an electron avalanche when the first electron arrives. For example, in some drift tubes, he avalanche of charge can be about 105 electrons per incoming electron that are easily detected with sensitive electronics. The anode wire 120 is connected to a readout circuit and is read-out electronically with the TDCS (time-to-digital converters) of the data acquisition electronics. As such, a hit signal is produced when a charged particle moves through the detector drift tube.

The examples described in this application can use various materials to construct the tube wall 110 that defines the ionization region 112. For example, aluminum and other metallic or electrically conductive materials can be used to construct the wall 110. For another example, other non-conductive materials, such as insulators, may also be used to construct the outer wall 110 and an electrically conductive layer or coating can be formed on the inner surface of the outer wall 110, such as carbon composite with internal conductive coatings. The drift tubes may be cylindrical with a circular cross section or in other geometries. For example, the drift tubes may be constructed from aluminum extrusions with multiple, non-circular cross-sections.

A signal processing unit can be coupled to receive and process data associated with the hit signal from the drift tube in FIG. 1. This signal processing unit can be integrated in the data acquisition circuit of the detector or can be remote from the detector. A hit signal includes data collected from the drift cell and represents: 1) time that the hit is collected by the electronics relative to a consistent but arbitrary origin, and 2) the drift cell channel number (or other identifier) for a detector using an array of drift tubes. The signal processing module can include a track reconstruction module that reconstructs the track of the charged particle passing through the detector and a calibration data base that calibrates the result. Predetermined drift cell positional information is stored in the calibration data base. The modules may be software or hardware.

As illustrated in FIG. 1, to track a cosmic ray-produced muon or other charged particle traveling through a given drift tube detector, a closest approach may be used in data processing. A "drift radius" as marked in FIG. 1 represents the closest distance between the path of a charged particle and the detector anode wire 120 running down the axis of the tube is determined. In some implementations, the path through the draft tube of a charged particle (e.g., a muon) can be approximated as a straight line because the deflection of the motion of the charged particle (e.g., muon) caused by the electrical field in the drift tube may be insignificant in such implementations. The moment of time that a charged particle (e.g., muon) passing through the drift tube causes ionization at a location on the charged particle track is the time zero (T0) and ionizations at different locations on the charged particle track have different values for the time zero (T0). Because charged particles (e.g., muons) move nearly at the speed of light, and much faster than the drifting electrons, it is a good approximation that any given charged particle passes through the entire apparatus instantaneously to cause ionization at different locations along the charged particle track in the drift tube at the same time which is the time the charged particle enters the drift tube. Under the above approximation, the time zero T0 is common to all of the hits in a given charged particle track. The time zero T0 can be determined for each charged particle track. The drift distance can be determined based on the travel time of the free electrons to the anode. This and other processing can be performed by the signal processing unit.

Figure 2:
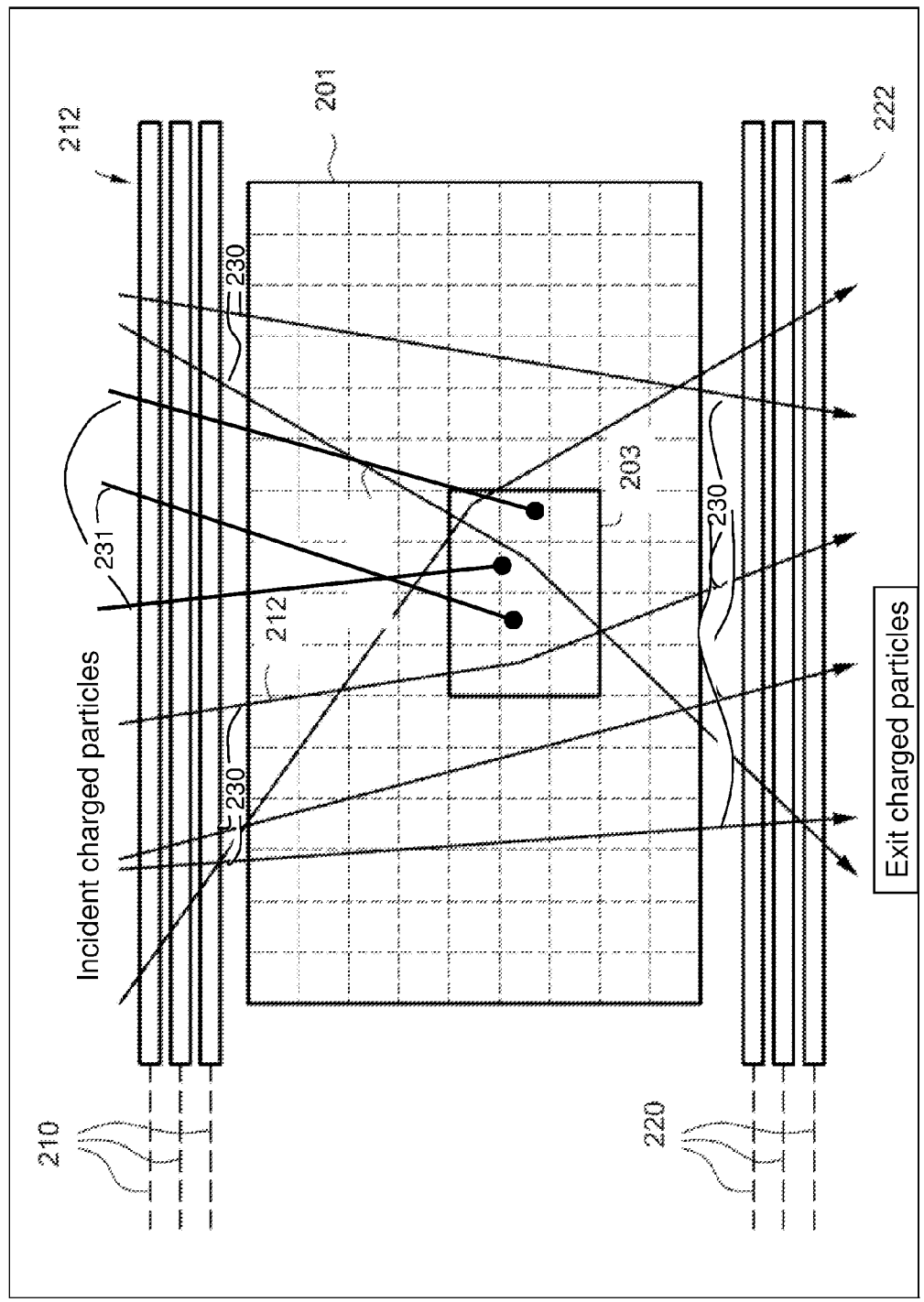
FIG. 2 shows an example of a muon tomography system based on gas chambers described in this application.

FIG. 2 shows an example of a muon tomography system based on gas chambers. The system in this example includes a set of two or more planes 210 of position-sensitive charged particle detectors 212 arranged above an object holding or inspection volume 201 to be imaged for providing the position and angles (i.e., directions in the 3-D space) of charged particle tracks 230 231. The charged particle detectors 212 are configured to measure the position and angles of charged particle tracks 230 231 with respect to two different directions, e.g., in two orthogonal coordinates along x and y axes. Charged particles (e.g., muons) pass through the volume 201 where the object 203 may be located and are scattered and lose energy to an extent dependent upon the material occupying the volume through which they pass. Another set of two or more planes 220 of position-sensitive charged particle detectors 222 are configured to record outgoing charged particle positions and directions 230 or the lack thereof 231. In some implementations, the drift tubes in detectors 212 and 222 in the two sets 210 and 220 are arranged to allow at least three charged particle positional measurements in a first direction and at least three charged particle positional measurements in a second direction which is different from the first direction and may be orthogonal to the first direction. Side detectors (not shown) may be used to detect more horizontally orientated charged particle tracks. In some implementations, additional side drift tube detectors can be implemented on sides of the volume 201 to form a box or four sided structure into which a package, a vehicle or cargo container can enter for scanning by the system. The scattering angle of each charged particle (e.g., muon) is computed from the incoming and outgoing measurements. As a specific example, each set of position sensitive detectors 210 or 220 can include a first double-layer of drift tubes arranged in the X direction and a second double-layer of drift tubes arranged in the Y direction. In each of the layers, the drift tubes can be arranged in two rows, offset by half a tube diameter from each other.

The system in the example in FIG. 2 includes a signal processing unit, e.g., a computer, to receive data of measured signals of the incoming charged particles 230 231 by the detectors 211 and outgoing charged particles (e.g., muons) 230 by the detectors 222.

This signal processing unit is configured to analyze the scattering and energy loss of the charged particles in the volume 201 based on the measured positions and directions of charged particles 230 231 to obtain a tomographic profile or the spatial distribution of the scattering density and energy loss reflecting the spatial distribution of materials within the volume 201. The obtained tomographic profile or the spatial distribution of the scattering density within the volume 201 can reveal the presence or absence of the object 203 in the volume 201.

The processing of measurements for cosmic ray-produced charged particles (e.g., muons) in a volume under inspection (e.g., a package, a container or a vehicle) by the processing unit for the system in FIG. B can include reconstructing the trajectory of a charged particle through the volume 201, measuring the momentum of an incoming charged particle based on signals from the detectors 212, measuring the momentum of an outgoing charged particle based on signals from the detectors 222, and determining the spatial distribution of materials in the volume 201. These and other processing results can be used to construct the tomographic profile and measure various properties of the volume 201.

For example, the reconstruction of the trajectory of a charged particle passing through a detector 212 or 222 having a set of drift tubes in FIG. 2 can include (a) receiving hit signals representing identifiers of drift cells hit by charged particles and corresponding hit times; (b) grouping in-time drift cell hits identified as being associated with a track of a particular charged particle passing through the detector; (c) initially estimating time zero for the particular charged particle; (d) determining drift radii based on estimates of time zero, drift time conversion data and the time of the hit; (e) fitting linear tracks to drift radii corresponding to a particular time-zero; and (f) searching and selecting a time-zero value associated with the best of the track fits performed for particular charged particle and computing error in time-zero and tracking parameters. Such reconstruction of the track based on the time zero fit provides a reconstructed linear trajectory of the charged particle passing through the charged particle detector without having to use fast detectors (such as photomultiplier tubes with scintillator paddles) or some other fast detector which detects the passage of the charged particle through the apparatus to the nearest few nanoseconds to provide the time-zero. Implementations for reconstruction of the trajectory of a charged particle are described in PCT Application No. PCT/US2007/082731 entitled "Determination of Trajectory of A Charged Particle" and filed on Oct. 26, 2007 (PCT Publication No. WO2008/118208), which is incorporated by reference as part of the specification of this application.

For another example, the processing for measuring the momentum of an incoming or outgoing charged particle based on signals from the detectors 212 or 222 in FIG. 2 can include (a) configuring a plurality of position sensitive detectors to scatter a charged particle passing therethrough; (b) measuring the scattering of a charged particle in the position sensitive detectors, wherein measuring the scattering comprises obtaining at least three positional measurements of the scattering charged particle; (c) determining at least one trajectory of the charged particle from the positional measurements; and (d) determining at least one momentum measurement of the charged particle from the at least one trajectory. This technique can be used to determine the momentum of the charged particle based on the trajectory of the charged particle which is determined from the scattering of the charged particle in the position sensitive detectors themselves without the use of additional metal plates in the detector. Implementations of techniques for determining the momentum of a charged particle are described in PCT Application No. PCT/US2007/082752 entitled "Measuring Momentum for Charged Particle Tomography" and filed on Oct. 26, 2007 (PCT Publication No. WO2008/140559), which is incorporated by reference as part of the specification of this application.

For yet another example, the spatial distribution of the scattering density of the volume 201 in FIG. 2 can be determined from charged particle tomographic data by: (a) obtaining predetermined charged particle tomography data corresponding to scattering angles and estimated energy loss of charged particles passing through object volume or charged particles stopping in a volume; (b) providing the probability distribution of charged particle scattering and energy loss for use in an expectation maximization (MUEM) algorithm, the probability distribution being based on a statistical multiple scattering and energy loss model; (c) determining substantially maximum likelihood estimate of object volume density using the expectation maximization (MUEM) algorithm; and (d) outputting reconstructed object volume spatial material distribution. The reconstructed object volume scattering density can be used to identify the presence and/or type of object occupying the volume of interest from the reconstructed spatial material distribution. Various applications include cosmic ray-produced charged particle tomography for various homeland security inspection applications in which vehicles or cargo can be scanned by a charged particle tracker. Implementations of techniques for determining the spatial distribution of the scattering density of a volume are described in PCT Application No. PCT/US2007/082753 entitled "Statistical Tomographic Reconstruction based on Measurements of Charged Particles" and filed on Oct. 26, 2007 (PCT Publication No. WO2008/140560), which is incorporated by reference as part of the specification of this application.

The tomographic processing part of the signal processing unit may be implemented in a computer at the same location as the detectors 212 and 222. Alternatively, the tomographic processing part of the signal processing unit may be implemented in a remote computer that is connected on a computer network such as a private network or a public network such as the Internet.

Thus, multiple scattering of cosmic ray-produced charged particles (e.g., muons) can be used to selectively detect high z-material in a background of normal cargo. Advantageously, this technique is passive, does not deliver any radiation dose above background, and is selective of high-z dense materials. As a charged particle traverses matter, it encounters Coulomb forces from each nucleon it passes and is deflected by the Coulomb forces. Each charged particle can be measured to provide the scattering angle of the charged particle trajectory as a measure of the integrated nuclear density along its path, the thickness of the material through which the charged particle has passed based on the distance of closest approach between linear extrapolations of the trajectory of the charged particle as it enters and leaves the volume of interest, and the location along the charged particles path where the scattering occurred as the point of closest approach between linear extrapolations of the charged particle's trajectory as it entered and left the volume of interest. Three-dimensional representations of the nuclear density in the volume of interest are generated from charged particle scattering data. The resolution of this reconstruction is determined by the number of charged particles passing through each resolution element (voxel). Studies have shown that in most scenes, approximately 7 to 10 charged particles traversing a voxel may be sufficient to distinguish at the level between low-Z filled voxels (concrete, water), medium-Z filled voxels (iron, copper) and high-Z filled voxels (tungsten, uranium). As an example, 5 cm voxels are traversed by 7 to 10 charged particles in approximately 20 seconds.

In addition to the above imaging based on detection of charged particles such as muons that penetrate through a volume of interest or under inspection, relatively "soft" charged particles, that have lower energy and are stopped inside the volume without penetrating through the volume, can also be detected to obtain information of the volume. This use of "soft" charged particles can be combined with the detection of the "hard" charged particles that penetrate through the volume to improve the overall imaging sensitivity a and sensing capability of the system (e.g., the system in FIG. B) that may be difficult to achieve by detecting either one type of the "hard" charged particles and the "soft" charged particles without detecting the other type.

When primary cosmic rays (protons, alpha particles, and heavier nuclei) strike the Earth's atmosphere, they produce cascades of various types of subatomic particles. The cosmic ray flux at the earth's surface is mainly a combination of muons and electrons. Muons originate from the decay of pions, while electrons and positrons are the product of muon decay, electron knock-out, and Bremsstrahlung. The flux of muons at sea level is approximately 1 $cm^{-2}$, and the electron flux is about 35-40% of the muons. Individual cosmic rays are usually classified as part of the soft or hard component of the spectrum. The soft component is defined as the part of the spectrum that is stopped by 15 cm of lead. Electrons and positrons dominate the makeup of the soft component.

The component of the cosmic ray flux that is sufficiently high in energy to pass through an object can be used for muon tomography (MT). Other background radiation induced processes that might provide information about unknown objects have also been studied. The soft component of the cosmic ray flux is not very penetrating and can provide additional information. In materials, charge particles are slowed and eventually stop because of the Coulomb interaction with electrons in the material. This process is sensitive to the electron density in the material through which the charge particles are passing. An analysis of the statistical precision of the information available from the stopping of cosmic rays, when the incident trajectories are measured, leads to the surprising discovery that it is more significant than the information from MT for thick objects.

Figure 3:
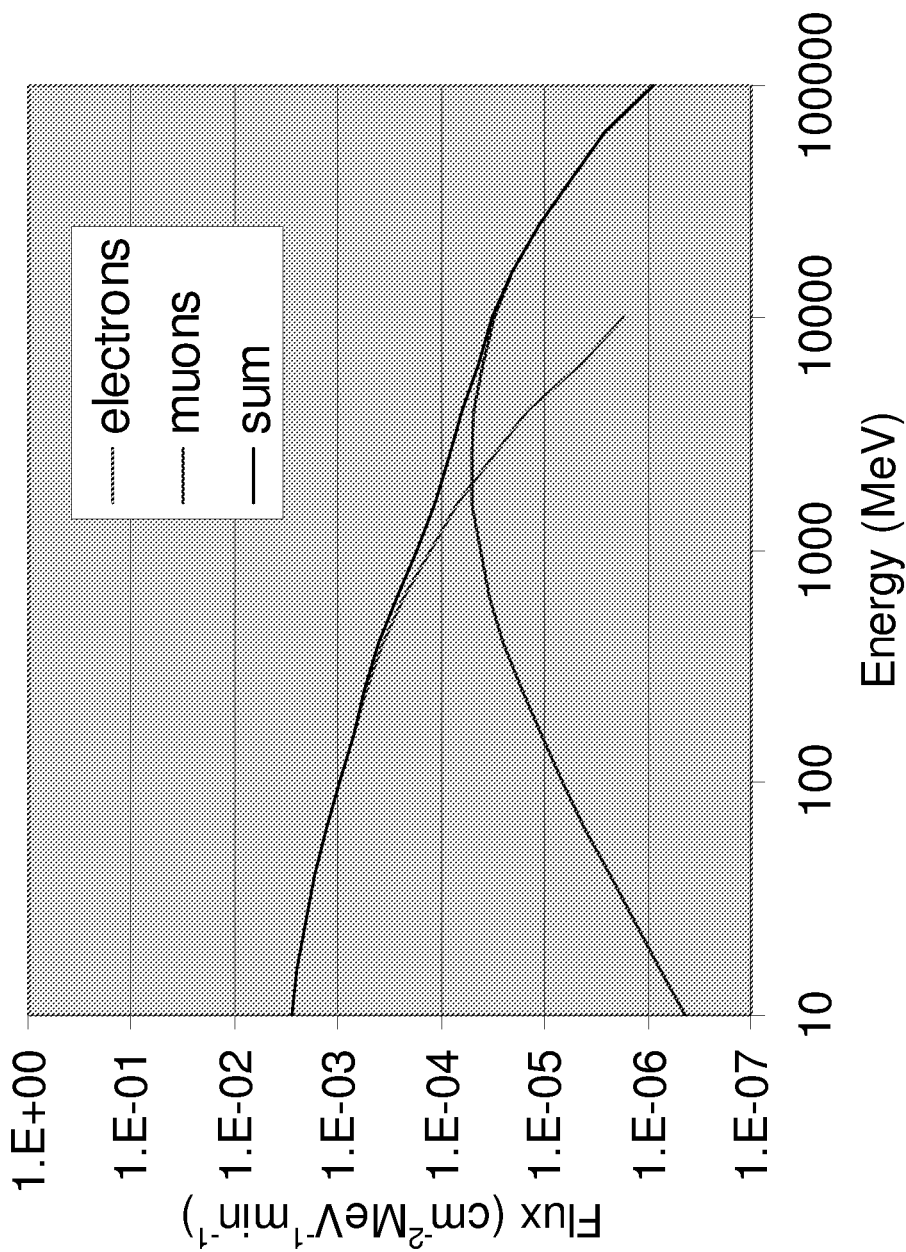
FIG. 3 an estimate of the sea level cosmic ray flux broken into its electron and muon components.

An estimate of the relative electron and muon fluxes as a function of energy is shown in FIG. 3. The energy integral muon component has been normalized to 1/cm²/minute and the electron component to 45% of this.

Figure 4:
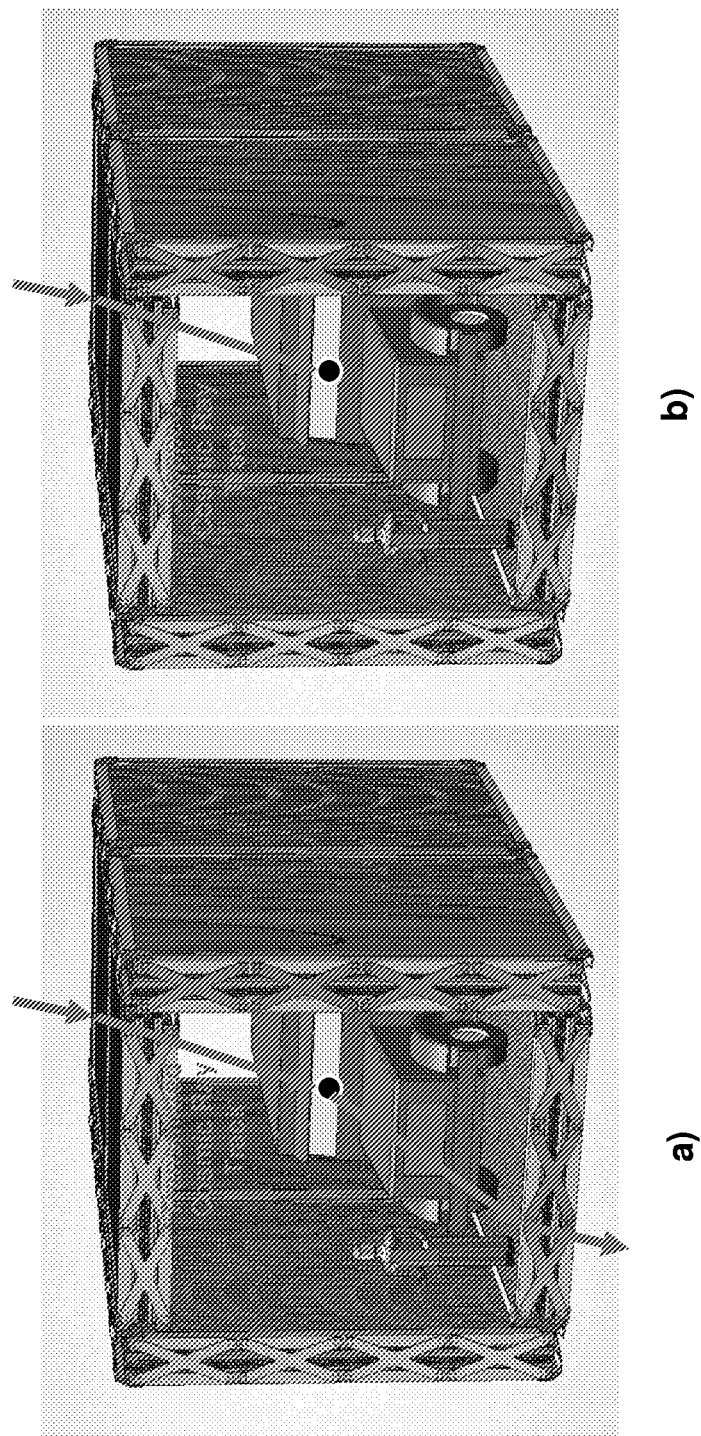
FIG. 4 shows an illustration of the two modes of using cosmic rays discussed in this paper. On the left (a) is an illustration of a transmitted cosmic ray and on the right (b) is an illustration of a stopped cosmic ray.

An MT scanner can be used to separate transmitted events from stopped events as shown in FIG. 4. In a), a cosmic ray comes in through the top detectors and out through the bottom detectors after passing through a threat object. In b), a cosmic ray stops in the threat object. The absence of signals from the low detector separates these stopped events from transmitted events. The tracking information from the entrance detectors enables tomography based on the stopping fraction expected for a model of the object given integral of the stopping power along the entrance trajectory. Multiple scattering in the entrance detector can be used to give a momentum estimate for the entering cosmic ray and this can be used to improve the estimate of the stopping fraction.

Counting Time Estimates

A 20 kg cube of high explosive with a density of 1.8 gm/cm³ and linear dimensions of 22 cm has been studied. This amount of explosives would be likely to cause catastrophic damage if it were detonated in a passenger rail car in a tunnel under the Hudson River. This object may be identifiable using the cosmic ray signals if its geometry can be constrained to suitable precision with tomographic techniques or by some other means such as optical imaging.

Conventional radiography takes advantage of the absorption of penetrating radiation. For X-ray radiography,[6] the areal density of an object is determined the absorption or scattering of the incident beam:

$$N_T = N_0 e^{-\frac{L}{L_0}}, \quad (1)$$

where L is the path length (areal density) through an object, and $L_0$ is the mean free path for scattering or absorption and $N_T$ and $N_0$ are the number of transmitted and incident particles respectively. Here we have assumed that all incident particles are described by the same mean free path, such as would be obtained with monoenergetic x-rays. The thickness of an object is given by:

$$L = L_0 \ln\left(\frac{N_T}{N_0}\right). \quad (2)$$

The uncertainty in the transmission is related tom the Poison statistics of the transmitted flux, $\Delta N_T = \sqrt{N_T}$, the only independent measured variable. If $r = N_T/N_0$, $\Delta r = \sqrt{N_T}/N_0$. The precision of radiographic measurement of L is $$\frac{\Delta L}{L_0} = \frac{\Delta r}{r} = \frac{1}{\sqrt{N_T}}. \quad (3)$$

With charged particles one can separately measure the transmitted flux, $N_T$, and the stopped flux, $N_S = N_0 - N_T$. This gives:

$$r = \frac{N_T}{N_T + N_S} \quad (4)$$

$$\Delta r = \sqrt{\frac{N_T N_S}{(N_T + N_S)}}$$

So:

$$\frac{\Delta L}{L_0} = \frac{1}{\sqrt{N_T}} \sqrt{\frac{N_S}{N_S + N_T}}. \quad (5)$$

Figure 5:
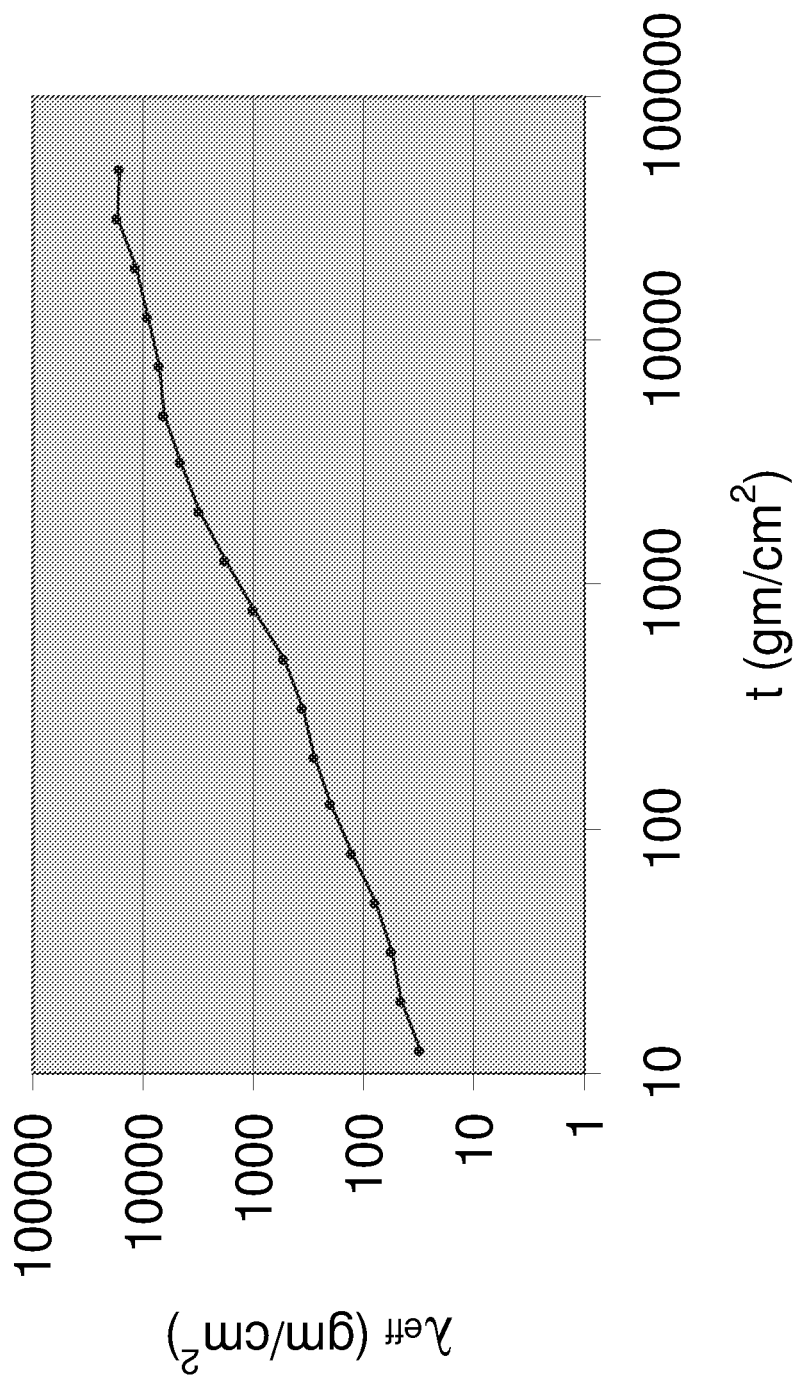
FIG. 5 shows an effective mean free path as a function of energy. This estimate has ignored electron showering, and has assumed an energy loss of 2 MeV/g/cm$^2$.

We see that measuring the incident flux results in a considerable statistical benefit when the transmission approaches unity ($N_S < N_T$). Here the attenuation can be locally modeled as an exponential where L0 is an effective mean free path, given by the inverse of the logarithmic derivative of the flux remaining after the path length of the object being interrogated:

$$L_0 = \frac{\int_{e(x)} N(E) dE}{\frac{d\left(\int_{e(x)} N(E) dE\right)}{dx}}.$$

Where N(E) is the cosmic ray flux as a function of energy, and E(x) is the energy lost in the distance x. We have plotted this for the sum of the hard and soft components of the cosmic ray flux in FIG. 5.

Complementary information is provided by multiple scattering radiography. Charged particles, such as protons or muons, interact with matter by multiple Coulomb scattering. The many small interactions add up to yield an angular deviation that follows a Gaussian distribution to a good approximation:

$$\frac{dN}{d\theta_x} = \frac{1}{\sqrt{2\pi}\,\theta_0} e^{-\frac{\theta_x^2}{2\theta_0^2}}. \quad (6)$$

The width of the distribution is related to the scattering material:

$$\theta_0 = \frac{14}{p\beta} \sqrt{\frac{X}{L}}, \quad (7)$$

where p is the particle momentum, β is the velocity divided by the velocity of light, and X is the radiation length. If the muon scattering angle in an object can be measured, and its momentum is known, then the path length, $\Delta l/l$ can be determined to a precision of $$\frac{\Delta l}{l} = \sqrt{\frac{2}{N_T}}. \quad (8)$$

It is assumed an incident cosmic ray flux (sum of electrons and muons) of 1.4/cm²/minute.

Figure 6:
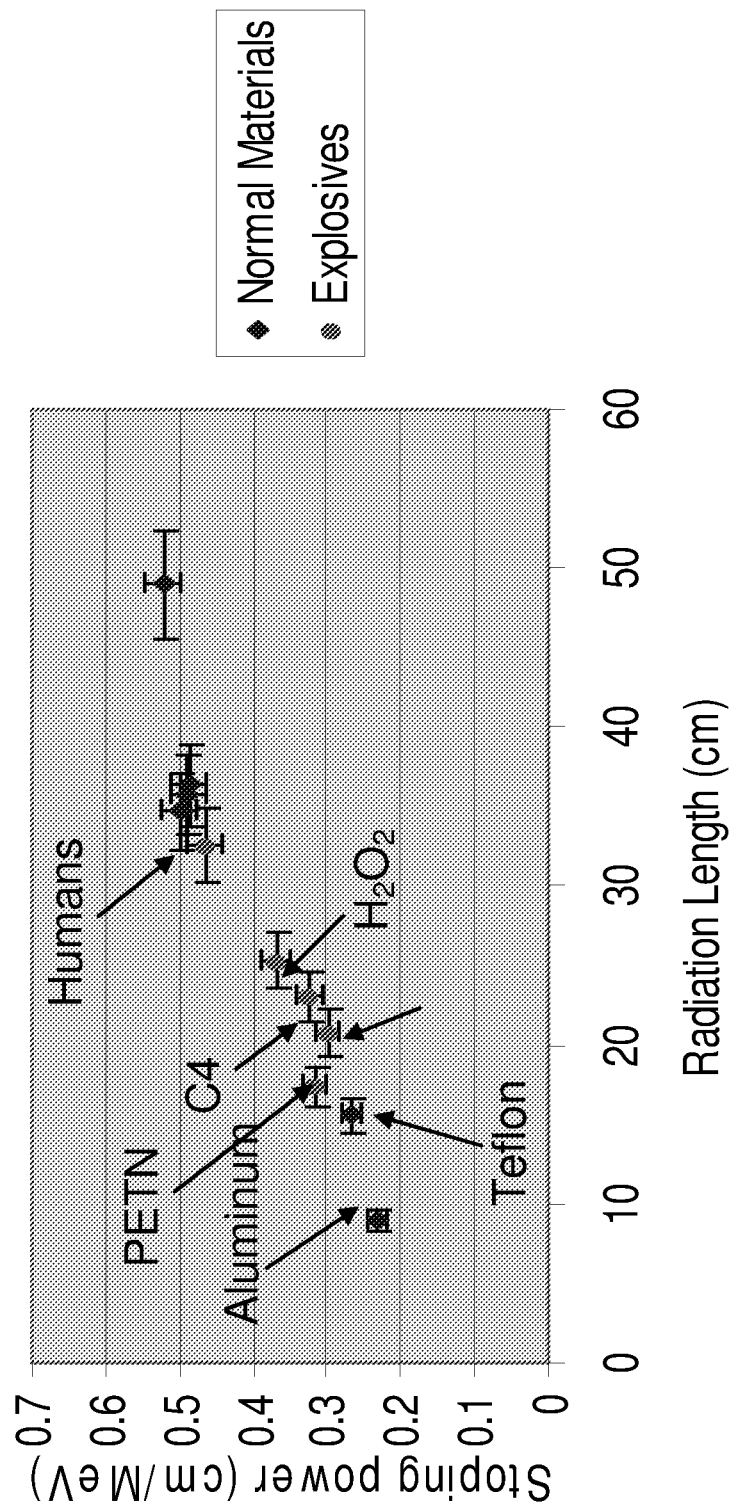
FIG. 6 shows a plot of the stopping power and radiation lengths for a set of normal materials and explosive materials along with the measurement error bars expected for a 22×22×22 cm$^3$ sized simple of these materials in a one minute exposure.

FIG. 6 shows the potential for cosmic ray measurement to be able to distinguish between some explosive materials and other normal materials. It is assumed that the properties of the solid materials can be extracted based on their geometry and the overburden materials are negligible. A four minute exposure reduces these errors by a factor of 2 and allows the different types of explosives to be distinguished.

Figure 7:
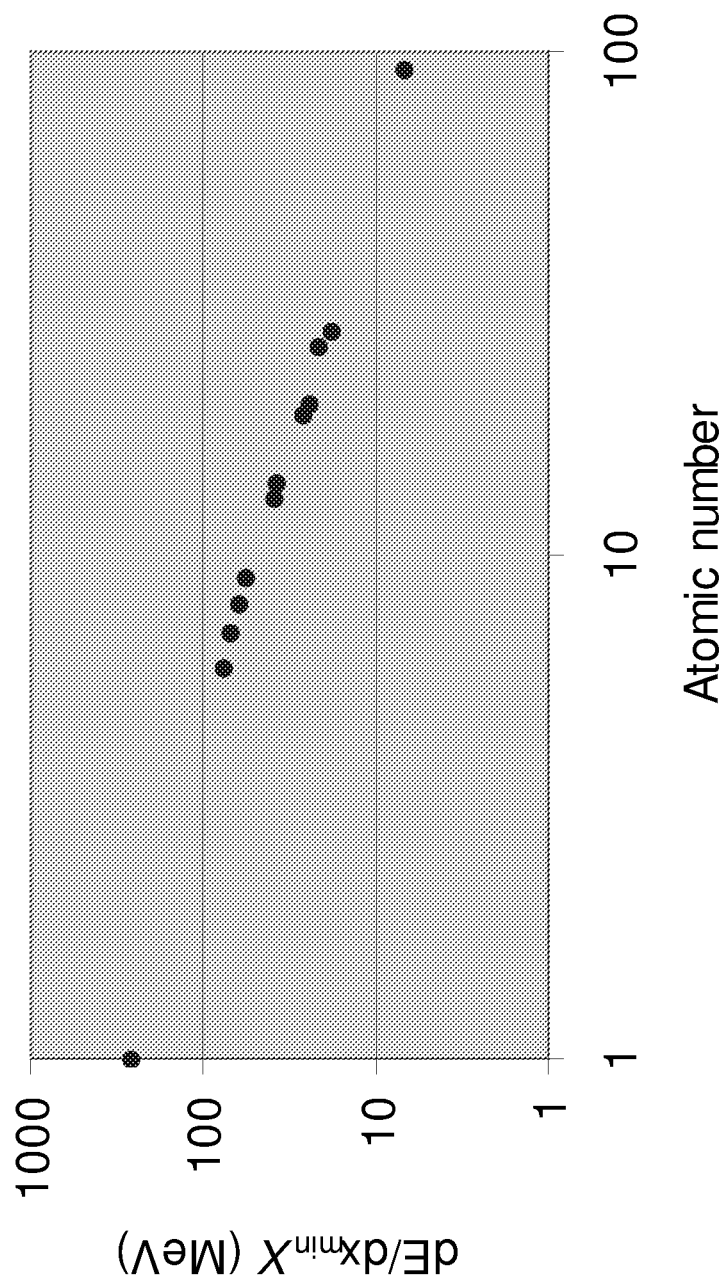
FIG. 7 shows the product of the minimum value of the energy loss (dE/dx) and radiation length is plotted across the periodic table.

FIG. 7 the product of the minimum value of the energy loss (dE/dx) and radiation length is plotted across the periodic table.

Another potential use of the stopping is to distinguish between different materials that may be configured to have the same density. It has been suggested that on method of thwarting muon tomography is to dilute uranium so that it has the same density as some innocuous material such as iron. Although the naïve model presented here suggests that distinguishing these should be trivial, mixtures of three materials can be fabricated that reproduce the density, radiation length and stopping power of any material bracketed by the surrogate materials. However, measuring stopping power makes it more difficult to spoof a cosmic ray scanner, and the composite objects require more shielding and need refabrication before the can be used as nuclear explosives.

In the above we have neglected to deal with electron showering. When objects are several radiation lengths or thicker, the transport of electrons becomes dominated by electromagnetic showering. In this case the incident energy is rapidly transformed into shower of particles. This will alter the stopping rates estimated above. Empirically determined stopping rates using suitably designed test objects will be required in the analysis of actual data, and may change some of the conclusions presented above.

Figure 8:
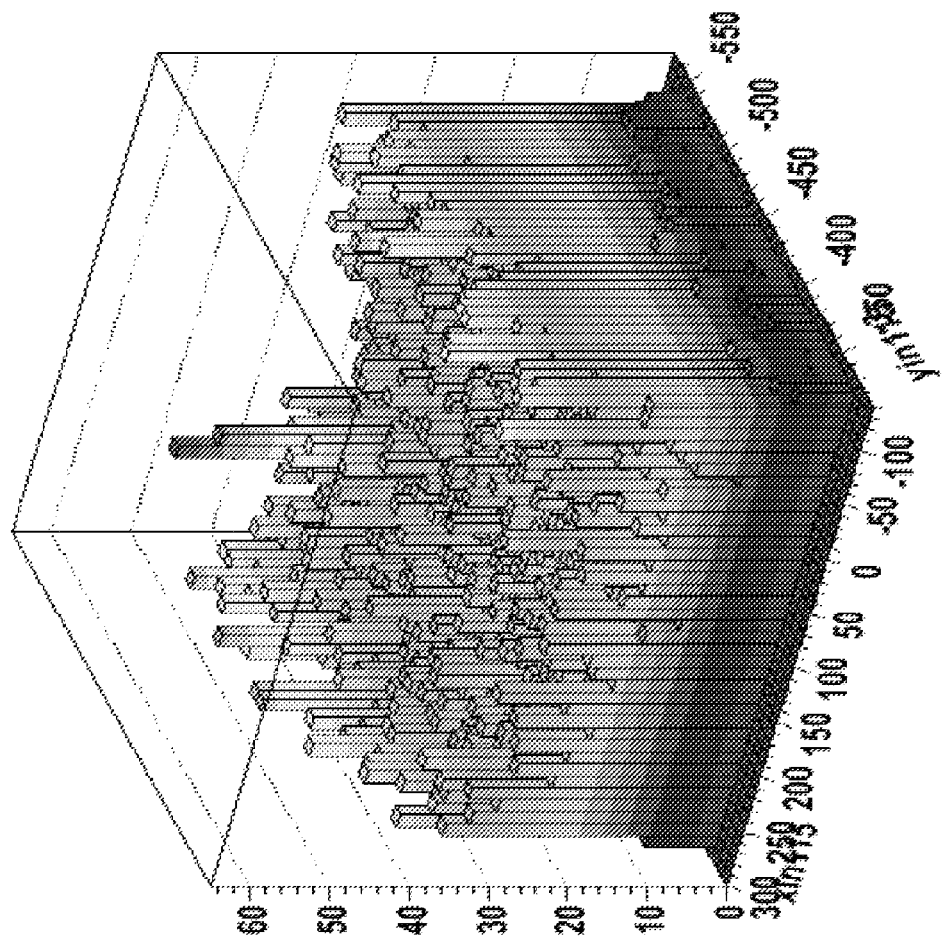
FIG. 8 shows a plot of the 2 dimensional distribution of stopped cosmic ray particles in a 20 kg block of Tungsten. The red peak represents the additional stopped particles in the tungsten block and is located at the X-Y position of the tungsten in the detector.

FIG. 8 A plot of the 2 dimensional distribution of stopped cosmic ray particles in a 20 kg block of Tungsten. The red peak represents the additional stopped particles in the tungsten block and is located at the X-Y position of the tungsten in the detector.

Object Reconstruction

The estimates presented above are geometrically over simplified. In reality the particle trajectory are not normal to the face of the cube but come from random directions and sample varying path lengths.

The information can be extracted for a three dimensional object illuminated from a randomly distributed flux by using a regularized maximum likelihood method, such has been used for single photon emission computed tomography (SPECT) reconstructions. A scene can be described as a set of voxelized densities, $\rho_{i,j,k}$. Here the densities are weighed by dE/dx, the stopping power for the material in the given voxel. If each cosmic ray, l, is described by a path length, $L_{likj}$, then the energy loss for a given cosmic ray $T_l$, is given by: $T_l = L_{lijk} \rho_{ijk}$. The probability that a given cosmic ray will stop can be approximately calculated as:

$$\mathcal{P}_l = \frac{\int_{T_l}^{\infty} \frac{dN}{dE} dE}{\int_{0}^{\infty} \frac{dN}{dE} dE}.$$

The likelihood function for a set of cosmic rays for which n have stopped and m have not stopped is:

$$L(\rho_{i,j,k}) = \prod_n \mathcal{P}_l \prod_m (1 - \mathcal{P}_l).$$

The 3-d image can be reconstructed by finding the $\rho_{i,j,k}$ that maximize the likelihood. Regularization methods can be used to damping fluctuations in situations where counting statistics limit the accuracy or even lead to an underdetermined solution to this problem. The product of the stopping and multiple-scattering likelihood can be solved simultaneously. In this case the stopping information is expected to provide important information about the low-density, low-z parts of the object. It is also expected to provide additional information to that available from the angular deflection signal about medium- and high-Z objects. In this case an addition parameter can be added to each voxel that gives the relative value of the stopping and radiation lengths. This problem appears to be non-linear, although linear approximations to the log-likelihood function may be found.

Therefore, for low areal mass scenes, the information contained in the cosmic ray stopping signal obtained from the "soft" charged particles is larger than that in the multiple scattering signal obtained from the "hard" charged particles. These two sources of information depend differently on atomic charge, so combining them allows both density and material identification. The extraction of tomographic information from the cosmic ray stopping requires solving a non-linear problem.

In addition to the multiple Coulomb scattering induced trajectory changes to charged particles traversing a volume of interest and the stopping of the charged particles inside the volume of interest, energy loss of penetrated charged particles (e.g., muons) can be characterized and used in tomographic reconstruction. Techniques for acquiring energy loss information from a charged particle tracking system are provided below and use this information in a tomographic reconstruction of the materials and their distribution within the volume of interest.

Charged particle tomography generates 3-dimensional pictures using the information contained in the multiple coulomb scattering that occurs as a charged particle passes through matter. As a charged particle traverses matter, it encounters Coulomb forces from each nucleon it passes. The more high atomic number nuclei the charged particle encounters, the more integrated scattering is possible. In addition to the detection of its trajectory, the charged particle loses some fraction of its energy according to its incident energy and the material through which it passes. The energy loss interaction is primarily an effect from the interactions of the particle with electrons in the material, rather than the scattering signal which is dominated by interactions with protons.

Referring to the system in FIG. 2, in addition to detecting the movement of charged particles in and out of the volume 201 of interest, the energy loss of the charged particles traversing the can be detected and analyzed. The charged particles enter the volume of interest 201 and interact with objects present in the trajectories of the charged particles. When the charged particles scatter in response to interacting with the objects, the charged particles lose energy based on the characteristics of the objects.

Figure 9:
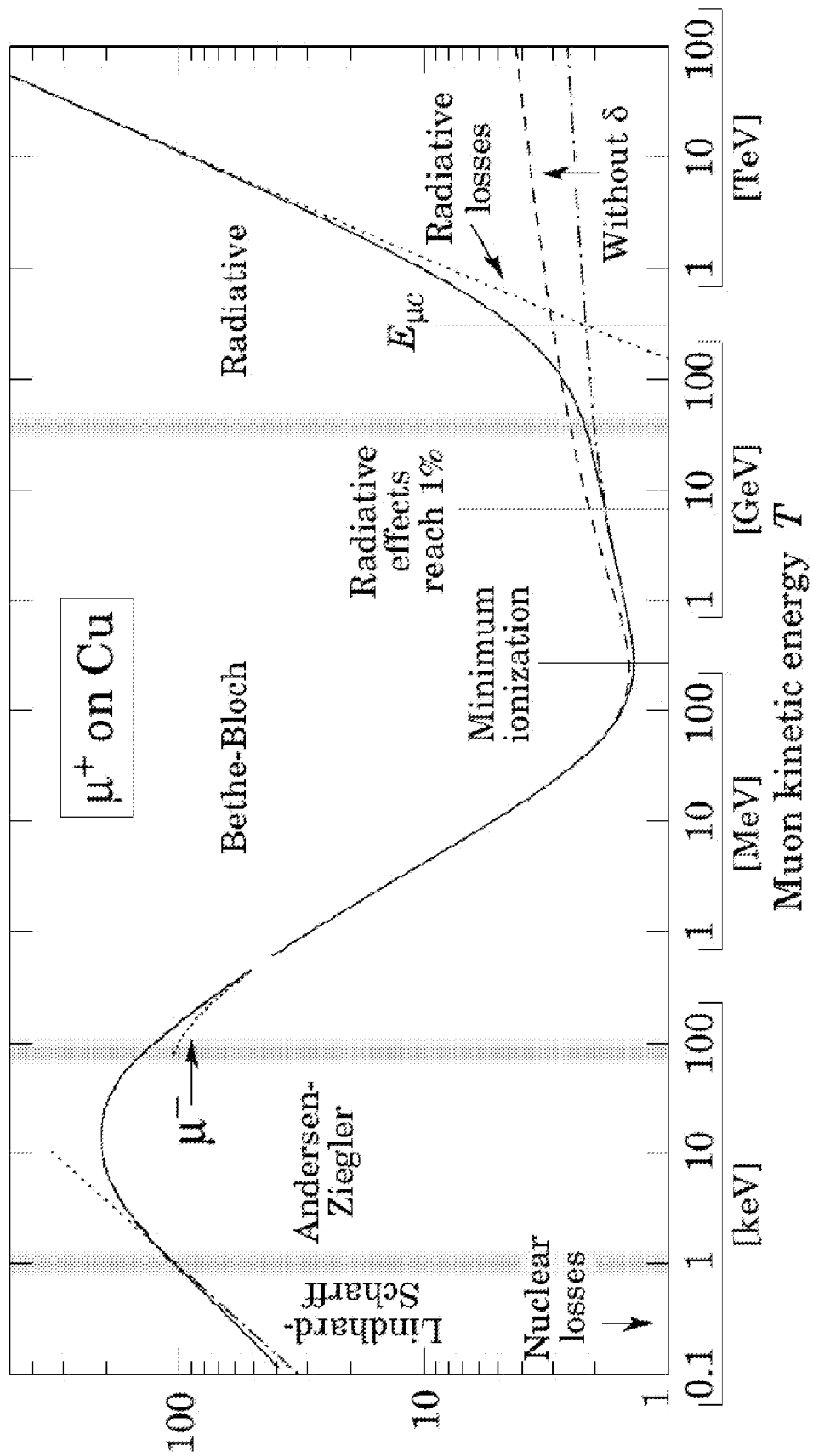
FIG. 9 shows an example of the stopping power for charged particles versus charged particle incident energy.

FIG. 9 shows an example of the stopping power for charged particles versus charged particle incident energy. An example stopping power (=(dE/dx)) is shown for positive muons in copper as a function of kinetic energy T (12 orders of magnitude range).

The energy loss is high for muons with kinetic energy at or below the rest mass of the muon (non-relativistic muons). Around the mean cosmic-ray muon kinetic energy of 4 GeV, the energy loss is described by Bethe's theory describing primarily ionization and excitation losses with some added corrections. Mean energy loss is approximately 2 MeV cm$^2$/g. Energy loss depends differently on atomic size and charge than multiple Coulomb scattering. Thus, a measurement of the energy loss, when combined with a multiple Coulomb scattering measurement, provides additional information about the materials in a volume of interest.

Figure 10:
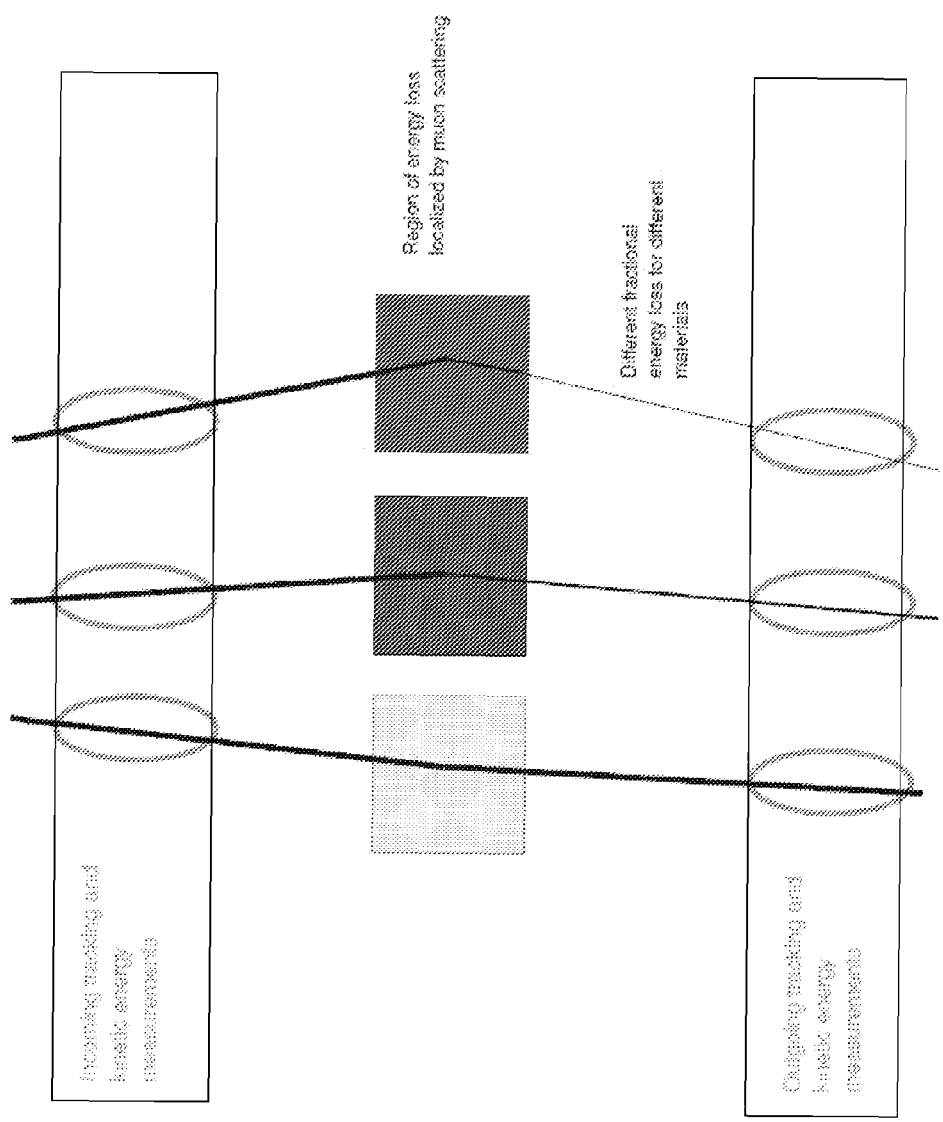
FIG. 10 shows an example illustration of the energy loss measurement in materials and how the measured loss probes properties of the materials in the volume of interest.

FIG. 10 shows an example illustration of the energy loss measurement in materials and how the measured loss probes properties of the materials in the volume of interest. Knowledge of the trajectory of the charged particle provides information on the position and distribution of materials causing the energy loss.

Measuring Energy Loss in a Charged Particle Tracking Detector

The momentum of a charged particle can be measured in a tracking detector according to its multiple scattering in the material comprising the detector. By evaluating the degree of agreement between the data produced by a charged particle and a straight line fit, an estimate of the momentum of the particle can be inferred. The momentum measurement can be made independently for the incoming and outgoing trajectories, providing a measurement of the energy lost while traversing the volume of interest.

Incorporating Energy Loss in Tomographic Reconstructions

Reconstruction programs are implemented to use voxels to define a volume of interest. Integers nx, ny and nz are used to define the sides x, y and z of an example rectangular volume. Each voxel includes sides dx, dy and dz with each side represented by a ratio of the side divided by the number n (i.e. dx=x/nx, etc.). Another parameter that can be used in reconstruction is a weighting factor assign to the voxels that result in an image when a 2D or 3D plot of the weighting factor versus the location of the voxels in space is generated.

The weighting factor can be considered as an average density of matter in each voxel. This is based on the weighting factor representing a measure of the average radiation length of matter in each voxel. The radiation length depends on the density and elemental charge of matter and is a measurable constant for each element that can be obtained from simulations of compounds of known elemental composition. Reconstruction algorithms can be implemented to assign weighting factors to the voxels based on the probe of the volume of interest that is being utilized.

For charged muons and electrons, the weighting factors can include scattering, energy loss, stopping, and showering as distinct processes that can be used for imaging of an interrogation volume. Weighting factors are added to voxels that are traversed by the charged particles and the sum of the weighting factors is related to the density or radiation length. Simple routines can be implemented to use the incoming trajectory and any outgoing trajectories of the charged particles that are measured by detectors (e.g., detectors 120 and 130) located on 2 sides of the volume of interest. More complicated routines can be implemented to use dynamic adjustments of the size of the voxels based on the density after the passage of a small sample of the charged particles; and smoothing or clustering based on the density of neighboring voxels.

In charged particle tomography (MT), three-dimensional representations of the scattering density, a measurement of density and atomic number (proton density) of the material in the volume of interest are generated from charged particle scattering data. The fidelity of this reconstruction is determined by the number of charged particles passing through each resolution element (voxel) and the amount of information available from each charged particle. The scattering angle, its location and the distance of closest approach between incoming and outgoing projections of the charged particle trajectory are included in a likelihood function. This function can be maximized according to the scattering data set to reconstruct the material properties and distribution in the volume of interest. Adding the energy loss of the charged particle to the likelihood function provides a related but partially independent measure of the electron density and distribution of materials in the volume of interest.

The update function is defined for each set of charged particles that pass through the volume of interest in a given time. This is considered to be one iteration. Each iteration is then added to a total number until the end of the scan. The update function is dependent on the number of voxels, the measurements that determine one or more weight factors. Each voxel is updated with some value calculated from the charged particles (e.g., muons and/or electrons) passing through the voxel, scattering angles and displacements. The information from showers can be added to this update function in each iteration. This way, all data is considered in the same likelihood calculation instead of calculating each (scattering and showering) separately. Other information that can be considered includes information from stopping and energy loss.

In implementation, the system in FIG. 2 can be used to obtain measured data containing information on penetrated charged particles (e.g., penetrated muons) and stopped charged particles that are trapped inside the volume of interest. Based on such information, the processing unit produces tomographic images of the volume based on different measurements and then produces a final image using one or a combination of at least two tomographic images.

Figure 11:
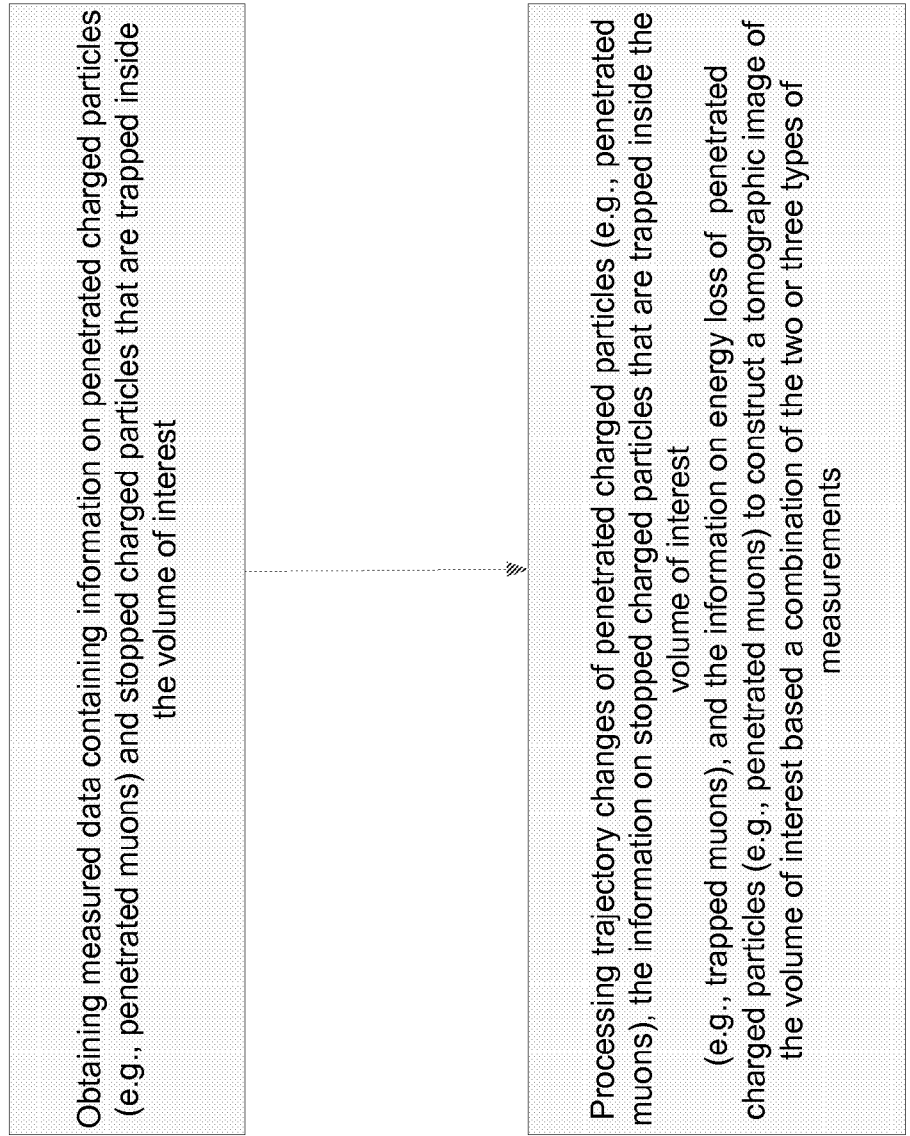
FIG. 11 shows an operation of the system in FIG. 2 based on information measured in both penetrated charged particles and trapped charged particles.

FIG. 11 shows an operation of the system in FIG. 2 based on information measured in both penetrated charged particles and trapped charged particles. Based on the measurements of the penetrated and stopped charged particles, the processing unit combines two or three types of measured data of trajectory changes of penetrated charged particles (e.g., penetrated muons), the information on stopped charged particles that are trapped inside the volume of interest (e.g., trapped muons), and the information on energy loss of penetrated charged particles (e.g., penetrated muons) to construct a tomographic image of the volume of interest. This process uses information of different processes inside the volume of interest to improve the fidelity and resolution of the final image for the volume of interest and to reduce the false detection. In one implementation, three types of measurements can be input into a processing algorithm to construct a single, maximum likelihood material tomographic map of the volume. As such, with the available three types of measurements from the system in FIG. 2, the generated tomographic image of the volume of interest can be more precise and accurate than the image from any of the measurements alone.

While this document contains many specifics, these should not be construed as limitations on the scope of any invention or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Thus, particular embodiments have been described. Variations and enhancements of the described embodiments and other embodiments can be made based on what is described and illustrated in this document.

What is claimed is what is described and illustrated, including:

1. A method for sensing a volume exposed to charged particles, comprising:
    measuring energy loss of charged particles that enter and penetrate the volume or are stopped inside the volume without penetrating through the volume;
    based on the measured energy loss, determining a spatial distribution of the charged particles that enter and penetrate the volume or are stopped inside the volume without penetrating through the volume;
    using the spatial distribution of the energy loss of the charged particles to reconstruct the three-dimensional distribution of materials in the inspection volume;
    measuring charged particles that enter and penetrate through the volume and those that stop in the volume; and
    combining measurements of the energy loss of charged particles with the angular deflection of charged particles to reconstruct the spatial distribution of one or more materials in the volume.

2. A tomography inspection system, comprising:
    a first set of position sensitive detectors located on a first side of an object holding area to measure positions and directions of incident charged particles entering the object holding area;
    a second set of position sensitive detectors located on a second side of the object holding area opposite to the first side to measure positions and directions of outgoing charged particles exiting the object holding area, or the absence of charged particles that have stopped in the volume; and
    a signal processing unit to receive data of measured signals of the incoming charged particles from the first set of position sensitive detectors and measured signals of the outgoing charged particles from the second set of position sensitive detectors, the signal processing unit configured to analyze behaviors of the charged particles caused by interactions with materials within the object holding area based on the measured incoming and outgoing positions and directions of charged particles to obtain a tomographic profile or the spatial distribution of materials within the object holding area,
    wherein the signal processing unit is operable to measure energy loss of charged particles that enter the volume and penetrate through the volume, and charged particles that are stopped inside the volume without penetrating through the volume, determine a spatial distribution of the charged particles that enter the volume and penetrate through the volume and charged particles that are stopped inside the volume without penetrating through the volume; and
    based on the measured energy loss, using the spatial distribution to reconstruct the spatial distribution of materials within the inspection volume.

3. A method for sensing a volume exposed to charged particles, comprising:
    using a first set of position sensitive detectors located on a first side of the volume to measure positions and directions of incident charged particles that penetrate the first set of position sensitive detectors to enter the volume;
    using a second set of position sensitive detectors located on a second side of the volume opposite to the first side to measure positions and directions of outgoing charged particles exiting the volume or the lack thereof;
    using measurements made by the second set of position sensitive detectors to determine incident charged particles that enter the volume and penetrate through the volume and charged particles that do not penetrate through the volume to reach the second set of position sensitive detectors;
    determining energy loss of charged particles that enter the volume and penetrate through the volume and charged particles that are stopped inside the volume without penetrating through the volume;
    determining a spatial distribution of the charged particles that enter the volume and are stopped inside the volume without penetrating through the volume, based on the measured energy loss; and
    using the spatial distribution of charged particles that enter the volume and are stopped inside to reconstruct the spatial distribution of materials in the inspection volume.

4. A method for sensing a volume exposed to charged particles, comprising:
    measuring energy loss of charged particles that enter the volume and are stopped inside the volume without penetrating through the volume;
    based on the measured energy loss, determining a spatial distribution of the charged particles that enter the volume and are stopped inside the volume without penetrating through the volume; and
    using the spatial distribution to detect presence of one or more low density materials with low atomic numbers.

5. The method as in claim 4, comprising:
    measuring charged particles that enter and penetrate through the volume to determine presence of one or more high density materials with atomic numbers higher than the low atomic numbers of one or more low density materials; and
    combining measurements of both the one or more high density materials and the one or more low density materials to inspect content inside the volume.

6. A tomography inspection system, comprising:
    a first set of position sensitive detectors located on a first side of an object holding area to measure positions and directions of incident charged particles towards the object holding area;
    a second set of position sensitive detectors located on a second side of the object holding area opposite to the first side to measure positions and directions of outgoing charged particles exiting the object holding area; and
    a signal processing unit to receive data of measured signals of the incoming charged particles from the first set of position sensitive detectors and measured signals of the outgoing charged particles from the second set of position sensitive detectors, the signal processing unit configured to analyze scattering behaviors of the charged particles caused by scattering of the charged in the materials within the object holding area based on the measured incoming and outgoing positions and directions of charged particles to obtain a tomographic profile or the spatial distribution of scattering centers within the object holding area, wherein the signal processing unit is operable to measure energy loss of charged particles that enter the volume and are stopped inside the volume without penetrating through the volume, determine a spatial distribution of the charged particles that enter the volume and are stopped inside the volume without penetrating through the volume, based on the measured energy loss, and use the spatial distribution to detect presence of one or more low density materials with low atomic numbers.

7. A method for sensing a volume exposed to charged particles, comprising:

using a first set of position sensitive detectors located on a first side of the volume to measure positions and directions of incident charged particles that penetrate the first set of position sensitive detectors to enter the volume;

using a second set of position sensitive detectors located on a second side of the volume opposite to the first side to measure positions and directions of outgoing charged particles exiting the volume;

using measurements made by the second set of position sensitive detectors to determine incident charted particles that enter the volume and do not penetrate through the volume to reach the second set of position sensitive detectors;

determining energy loss of charged particles that enter the volume and are stopped inside the volume without penetrating through the volume;

determining a spatial distribution of the charged particles that enter the volume and are stopped inside the volume without penetrating through the volume, based on the measured energy loss; and using the spatial distribution to detect presence of one or more low density materials with low atomic numbers inside the volume.

8. The method as in claim 7, comprising:

measuring charged particles that enter and penetrate through the volume to determine presence of one or more high density materials with atomic numbers higher than the low atomic numbers of one or more low density materials; and combining measurements of both the one or more high density materials and the one or more low density materials to inspect content inside the volume.

9. The method as in claim 1, further comprising:

using comic ray produced muons that naturally exist on the earth surface as a source of the charged particles without using an artificial radiation source to generate the charged particles in sensing the volume.

10. The method as in claim 9, further comprising:

using measurements of energy loss of only the charged particles that enter and penetrate the volume, without using measurements of the energy loss of the charged particles that are stopped inside the volume without penetrating through the volume, to reconstruct the spatial distribution of one or more materials in the volume.

11. The method as in claim 9, further comprising:

using measurements of energy loss of only the charged particles that are stopped inside the volume without penetrating through the volume, without using measurements of the energy loss of the charged particles that enter and penetrate the volume, to reconstruct the spatial distribution of one or more materials in the volume.

12. The method as in claim 11, further comprising:

using measurements of energy loss of electrons that are produced by the comic ray produced muons inside the volume and that are stopped inside the volume without penetrating through the volume, to reconstruct the spatial distribution of one or more materials in the volume.

13. The method as in claim 11, further comprising:

using measurements of energy loss of positrons that are produced by the comic ray produced muons inside the volume and that are stopped inside the volume without penetrating through the volume, to reconstruct the spatial distribution of one or more materials in the volume.

14. The system as in claim 2, wherein:

the system uses comic ray produced muons that naturally exist on the earth surface as a source of the incident charged particles to the object holding area without using an artificial radiation source.

15. The method as in claim 3, further comprising:

using comic ray produced muons that naturally exist on the earth surface as a source of the charged particles without using an artificial radiation source to generate the charged particles in sensing the volume.

16. The method as in claim 4, further comprising:

using comic ray produced muons that naturally exist on the earth surface as a source of the charged particles without using an artificial radiation source to generate the charged particles in sensing the volume.

17. The system as in claim 6, wherein:

the system uses comic ray produced muons that naturally exist on the earth surface as a source of the incident charged particles to the object holding area without using an artificial radiation source.

* * * * *